(12) United States Patent
Baxter

(10) Patent No.: US 7,915,303 B2
(45) Date of Patent: Mar. 29, 2011

(54) GLYCOPYRRONIUM SALTS AND THEIR THERAPEUTIC USE

(75) Inventor: Andrew Douglas Baxter, Cambridge (GB)

(73) Assignee: Sosei R&D Ltd., Essex (GB)

( * ) Notice: Subject to any disclaimer, the term of this patent is extended or adjusted under 35 U.S.C. 154(b) by 268 days.

(21) Appl. No.: 11/908,714

(22) PCT Filed: Mar. 20, 2006

(86) PCT No.: PCT/GB2006/000995
§ 371 (c)(1),
(2), (4) Date: Jul. 3, 2008

(87) PCT Pub. No.: WO2006/100453
PCT Pub. Date: Sep. 28, 2006

(65) Prior Publication Data
US 2009/0062372 A1      Mar. 5, 2009

(30) Foreign Application Priority Data

Mar. 24, 2005   (GB) .................................. 0506127.0
Mar. 24, 2005   (GB) .................................. 0506129.6
Nov. 16, 2005   (GB) .................................. 0523354.9

(51) Int. Cl.
*A61K 31/40* (2006.01)
*A61P 11/00* (2006.01)
*C07D 207/12* (2006.01)

(52) U.S. Cl. ........................................ 514/424; 548/556
(58) Field of Classification Search .................. 514/424; 548/556

See application file for complete search history.

(56) References Cited

U.S. PATENT DOCUMENTS 7,229,607 B2 *   6/2007   Bannister et al. ............... 424/45
2002/0173536 A1 *  11/2002   Noe et al. ...................... 514/424
2003/0068280 A1    4/2003   Bannister et al.

FOREIGN PATENT DOCUMENTS

EP          1 616 567       1/2006

* cited by examiner

*Primary Examiner* — Yong Chu
(74) *Attorney, Agent, or Firm* — Saliwanchik, Lloyd & Eisenschenk

(57) ABSTRACT

A glycopyrronium salt such as glycopyrronium iodide has a lower glass transition temperature than glycopyrronium bromide. It is therefore more suitable for formulation.

3 Claims, No Drawings

GLYCOPYRRONIUM SALTS AND THEIR THERAPEUTIC USE

This application is a National Stage Application of International Application Number PCT/GB2006/000995, filed Mar. 20, 2006; which claims priority to Great Britain Applications Nos. 0506129.6, filed Mar. 24, 2005; 0506127.0, filed Mar. 24, 2005; and 0523354.9, filed Nov. 16, 2005.

FIELD OF THE INVENTION

The present invention relates to the manufacture, characterisation and therapeutic use of glycopyrronium salts.

BACKGROUND TO THE INVENTION

Glycopyrronium bromide is a long acting anti-muscarinic agent currently under development for the treatment of respiratory disorders such as chronic obstructive pulmonary disease (COPD). See for example, WO01/76575.

Part of the development of glycopyrronium bromide involves milling of the active substance down to a particle size suitable for use in a dry powder inhalation formulation. During the course of formulation development it has been found that small pockets of amorphous glycopyrronium bromide formed on the surface of milled particles lead to substantial agglomeration and fusion of these particles, creating larger particles that are unsuitable for inhaled delivery. Characterisation of the amorphous form of glycopyrronium bromide reveals that the solid is highly hygroscopic. This material becomes sticky upon sorption of moisture at low relative humidity (RH), and then finally crystallises to a non-hygoscopic hard crystalline substance.

The glass transition temperature (Tg) of amorphous glycopyrronium bromide, as determined by differential scanning calorimetry (DSC), is relatively low at 64.9° C. Moisture adsorbed by the amorphous material acts as a plasticizer, lowering the glass transition temperature to ambient temperature at low RH. Clearly, milled substance which contains part amorphous and part crystalline material is not in a stable physical form at ambient temperature and low RH. This complexity means that it is difficult to achieve batch-to-batch consistency in the milling process, resulting in formulations with variable performance when applied to a dry powder inhaler (DPI).

SUMMARY OF THE INVENTION

The present invention is based on observation that, whereas glycopyrronium chloride apparently does not, certain glycopyrronium salts (2), such as the iodide, acetate or sulphate, have a lower glass transition temperature (Tg) than glycopyrronium bromide (1)

X = Br (1)
X = I, HSO$_4$, OCOCH$_3$ (2)

On milling, these novel salts result in a stable physical form suitable for formulation. Such formulations are in turn suitable for use in a dry powder inhaler (DPI) and can be used for the treatment of respiratory diseases such as COPD and asthma.

DESCRIPTION OF THE INVENTION

Salts of the invention may include a counter-ion which has the formula OCO(CH$_2$)$_n$CH$_3$ where n is zero or an integer of 1 to 10. The iodide, acetate and sulphate salts are used for the purposes of illustration, and are exemplified below. In general, the Tg of a novel salt may be below 60° C., e.g. down to 55, 50, 45, 40, 35, 30° C. or below.

It will be appreciated that the compounds according to the invention contain one or more asymmetrically substituted carbon atoms. The presence of one or more of these asymmetric centres in a compound of formula (2) can give rise to stereoisomers, and in each case the invention is to be understood to extend to all such stereoisomers, including enantiomers and diastereomers, and mixtures including racemic and non-racemic mixtures thereof. In the case of new glycopyrronium salts (2), for example, this covers diastereoisomers of glycopyrronium iodide, sulphate or acetate either as individual single enantiomers, or as racemic or non-racemic mixtures of the R,R/S,S or R,S/S,R pairs of diastereoisomers, or as a mixture of all four diastereoisomers in various proportions.

Glycopyrronium iodide, for example, may be prepared by a route analogous to that reported in U.S. Pat. No. 2,956,062 for the manufacture of glycopyrronium bromide, utilising N-methylpyrrolidin-3-ol (NMP) and methyl hydroxycyclopentylmandelate (MCPM), as shown in the following scheme.

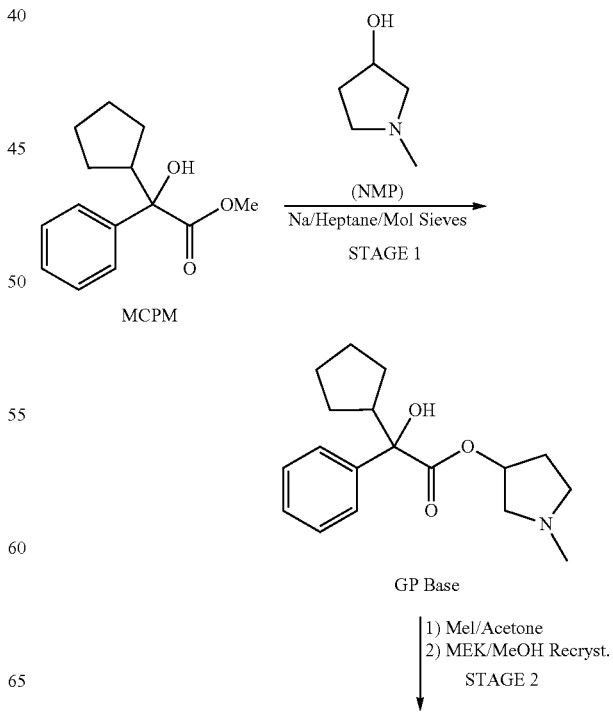

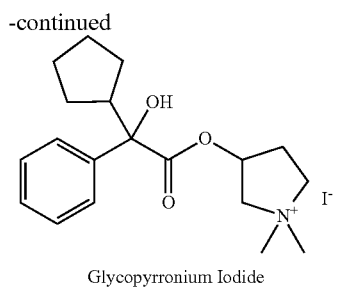

Glycopyrronium Iodide

Modification of this route utilising methyl iodide or dimethylsulphate in stage 2 also forms part of the invention, as control of particle size in the final crystallisation stages leads to a finer product more suitable for micronisation and subsequent formulation.

It will be appreciated that where a particular stereoisomer of formula (2) is required, the synthetic processes described herein may be used with the appropriate homochiral starting materials and/or isomers maybe resolved from mixtures using conventional separation techniques (e.g. HPLC).

It will also be appreciated that glycopyrronium bromide (1) and stereoisomers thereof can used as a starting material in the manufacture of glycopyrronium salts (2) where, for example, ion-exchange techniques can be used to exchange bromide for iodide. Other glycopyrronium salts (2) are prepared by treating glycopyrronium bromide (1) with the silver salt of the desired counterion. In this way glycopyrronium sulphate can be prepared using silver sulphate and glycopyrronium acetate by using silver acetate. In principle this latter technique could be used to prepared any organic salt of glycopyrronium, providing the silver salt can be manufactured. Thus, another asset of the invention is congeners of acetate such as propionate, butyrate and the like.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

Glycopyrronium salts (2) exhibit more stable physical characteristics than glycopyrronium bromide (1). The amorphous form of glycopyrronium iodide (2), for example, can be formed by physical techniques such as spray drying or lyophylisation and its sorption behaviour studied by dynamic vapour sorption (DVS) varying RH over time.

Glycopyrronium salts according to the invention exhibit in vitro antagonist activity at the muscarinic receptor subtypes (M1, M2, M3, M4 and M5). The compounds according to the invention also exhibit in vitro relaxation of tracheal strip preparations. The activity of the compounds may be determined by use of the appropriate assays well known to those skilled in the art.

This invention also relates to a method of treatment for patients (including man and/or mammalian animals raised in the dairy, meat or fur industries or as pets) suffering from disorders or diseases which can be attributed to muscarinic activity, and more specifically, a method of therapy (by which is meant treatment or prophylaxis) involving the administration of the muscarinic antagonist of formula (2) as the active constituent. Accordingly, the compounds of formula (2) can be used among other things in the treatment of respiratory diseases, such as chronic obstructive pulmonary disease (COPD) and asthma, smooth muscle disorders, such as urinary incontinence and irritable bowel syndrome and skin diseases, such as psoriasis.

The diseases or conditions referred to above include respiratory diseases such as chronic obstructive pulmonary disease (COPD) or asthma where the preferred route of administration is by inhalation or aspiration. Glycopyrronium salts (2) have particular advantages (described above) over the corresponding bromide (1) in the preparation of a formulation suitable for use in a dry powder inhaler (DPI). Such a formulation contains suitable diluents or carrier molecules, such as lactose and may contain performance enhancing agents, such as magnesium stearate.

For the treatment of systemic diseases resulting from the over-activity of acetylcholine such as smooth muscle disorders (i.e. urinary incontinence and irritable bowel syndrome) or skin disorders (such as psoriasis) glycopyrronium salts (2) may be administered orally, topically, parenterally, by nasal spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in U.S. Pat. Nos. 4,256,108, 4,166,452 and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydroxypropylmethylcellulose, sodium alginate polyvinylpyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a to demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium iodide solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (2) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of formula (2) are employed. For purposes of this specification, topical application includes mouth washes and gargles.

Dosage levels of the order of from about 0.1 µg to about 25 mg per kilogram of body weight per day are useful in the treatment of the above-indicated conditions (about 8 µg to about 2 g per patient per day). For example, COPD may be effectively treated by the administration of from about 0.25 to 12.5 µg of the compound per kilogram of body weight per day (about 20 µg to about 1 mg per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples 1 to 3 illustrate the invention.

EXAMPLE 1

Glycopyrronium Iodide 245 mg of the bromide salt were dissolved in 35 ml of dichloromethane. 2 ml of a 20% NaI solution were added and the system was allowed to phase separate and the organic phase was collected after standing for 16 hours. The solvent was evaporated by passing a gentle nitrogen stream over the solution, and glycopyrronium iodide was obtained as a white powder.

Elemental analysis: complies; NMR: complies; Raman: complies; TG-FTIR: no significant weight loss below 200° C., degrades above this temperature.

Glycopyrronium iodide (lyophilized): DSC first scan: Tm (peak): 186.6° C. (melting), second scan: Tg: 55° C. (glass transition).

EXAMPLE 2

Glycopyrronium Acetate

Following the same general procedure, 1 g (2.5 mmol) of glycopyrronium bromide was dissolved in water (10 ml) at room temperature. A suspension of silver acetate (1 equiv.) in water (10 ml) was added. The resulting mixture was then stirred for 20 hours at room temperature, filtered through a pad of Celite and evaporated to dryness to provide glycopyrronium acetate as a white solid.

Elemental analysis: complies; NMR: complies; Raman: complies; TG-FTIR: no significant weight loss below 200° C., degrades above this temperature.

EXAMPLE 3

Glycopyrronium Sulphate

Glycopyrronium sulphate was prepared according to the same general procedure, using silver sulphate instead of silver acetate. The compound was obtained as a white solid.

Elemental analysis: complies; NMR: complies; Raman: complies; TG-FTIR: no significant weight loss below 200° C., degrades above this temperature.

The invention claimed is:

1. A glycopyrronium iodide, as a pair of diastereoisomers, having a glass transition temperature of 55° C.

2. The glycopyrronium iodide according to claim 1, in milled form.

3. A dry powder inhaler comprising a glycopyrronium iodide according to claim 1.

* * * * *